(12) United States Patent
Prinz

(10) Patent No.: US 7,053,068 B2
(45) Date of Patent: May 30, 2006

(54) CHITOSAN-THIO-AMIDINE CONJUGATES AND THEIR COSMETIC AS WELL AS PHARMACEUTIC USE

(75) Inventor: Martin Prinz, Leobendorf (AT)

(73) Assignee: Mucobiomer Biotechnologische Forschungs- und Entwicklungs GESmbH, Leobendorf (AT)

( * ) Notice: Subject to any disclaimer, the term of this patent is extended or adjusted under 35 U.S.C. 154(b) by 187 days.

(21) Appl. No.: 10/487,721

(22) PCT Filed: Jun. 7, 2002

(86) PCT No.: PCT/EP02/06250

§ 371 (c)(1),
(2), (4) Date: Feb. 27, 2004

(87) PCT Pub. No.: WO03/020771

PCT Pub. Date: Mar. 13, 2003

(65) Prior Publication Data

US 2004/0236095 A1 Nov. 25, 2004

(30) Foreign Application Priority Data

Aug. 31, 2001 (AT) ............... A 1384/2001

(51) Int. Cl.
*A01N 43/04* (2006.01)
*C07H 5/04* (2006.01)
*C08B 37/00* (2006.01)

(52) U.S. Cl. ............... 514/55; 514/54; 536/55.1; 536/20; 536/55.3

(58) Field of Classification Search ............... 514/55, 514/54; 536/20, 55.1, 55.3
See application file for complete search history.

(56) References Cited

U.S. PATENT DOCUMENTS 5,248,772 A 9/1993 Siiman et al. ............... 536/112

FOREIGN PATENT DOCUMENTS

| | | |
|---|---|---|
| DE | 3432227 | 3/1986 |
| EP | 0 665 022 | 8/1995 |
| WO | WO 95/22315 | 8/1995 |
| WO | WO 98/31712 | 7/1998 |
| WO | WO 00/71136 | 11/2000 |
| WO | WO 00/71180 | 11/2000 |
| WO | WO 01/55220 | 8/2001 |

OTHER PUBLICATIONS

Alejandro et al., "Activation of polysaccharides with 2-iminothiolane and its uses," *Biochemistry*, 19:4341-4345, 1980.

Illum, "Chitosan and its use as pharmaceutical excipient," *Pharmaceutical Research*, 15(9):1326-1331, 1998.

Naidoo, "Natural cosmetic constituents: seaweed, chitosan and rice," *South African Pharmaceutical Journal*, 59(6):131-132, 1992.

Tarentino et al., "2-iminothiolane: a reagent for the introduction of sulphydryl groups into oligosaccharides derived from asparagine-linked glycans," *Glycobiology*, 3(3):279-285, 1993.

Thanou et al., "Mono-N-carboxymethyl chitosan (MCC), a polyampholytic chtosan derivative, enhances the intestinal absorption of low molecular weight heparin across intestinal epithelia in vitro and in vivo," *J. Pharm. Sci.*, 90(1):38-46, 2001.

Thanou et al., "N-Trimethylated chitosan chloride (TMC) improves the intestinal permeation of the peptide drug Buserelin invitro (Caco-2 cells) and in vivo (rats)," *Pharmaceutical Research*, 17(1):27-31, 2000.

*Primary Examiner*—Samuel Barts
*Assistant Examiner*—Michael C. Henry
(74) *Attorney, Agent, or Firm*—Fulbright & Jaworski L.L.P.

(57) ABSTRACT

By the reaction of chitosan with iminothiolactones such as 2-iminothiolane, thiol groups can be covalently immobilized on the polymer. The resulting chitosan derivatives exhibit thiol groups which are capable of forming inter- and intramolecular disulfide bonds. Because of this crosslinking process the viscosity of polymer solutions is strongly improved. Moreover, the cationic character of the polymer is strongly improved. Preferred applications of these novel chitosan derivatives are their cosmetic and pharmaceutical use

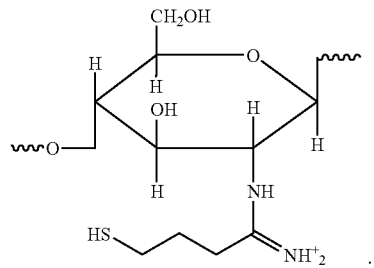

31 Claims, 2 Drawing Sheets

CHITOSAN-THIO-AMIDINE CONJUGATES AND THEIR COSMETIC AS WELL AS PHARMACEUTIC USE

This application is a national phase application under 35 U.S.C. § 371 of PCT Application No. PCT/EP02/06250 filed 7 Jun. 2002, which claims priority to Austrian Application No. A 1384/2001 filed 31 Aug. 2001, the contents of which are incorporated herein by reference in their entirety.

The use of polymeric compounds in cosmetic and pharmaceutical formulations has a long tradition. At the beginning only polymers from natural sources such as starch and gelatin were used. The development of organic chemistry led then to the generation of synthetic polymers such as polyacrylates. Moreover, due to the chemical modification of natural polymers, their features could also be strongly improved. The generation of cellulose ethers, for instance, resulted in novel cosmetically and pharmaceutically used polymers exhibiting strong gelling properties in aqueous solutions. Another invention was the deacetylation of chitin, which can be isolated from crab shells. Deacetylated chitin or so-called chitosan is used as gelling polymer in cosmetic [Naidoo, N. T., Natural cosmetic constituents: seaweed, chitosan and rice. S. Afr. Pharm. J.; 59 (1992) 131–132] as well as pharmaceutical formulations [Illum, L., Chitosan and its use as a pharmaceutical excipient. Pharm. Res. 15 (1998) 1326–1331]. Chemically modifications of chitosan resulted in trimethylated chitosan [Thanou, M., Florea, B. I., Langemeyer, M. W., Verhoef, J. C., Junginger, H. E., N-trimethylated chitosan chloride (TMC) improves the intestinal permeation of the peptide drug buserelin in vitro (Caco-2 cells) and in vivo (rats). Pharm. Res. 17 (2000) 27–31], mono-N-carboxymethyl chitosan [Thanou, M., Nihot, M. T., Jansen, M., Verhoef, J. C., Junginger, H. E., Mono-N-carboxymethyl chitosan (MCC), a polyampholytic chitosan derivative, enhances the intestinal absorption of low molecular weight heparin across intestinal epithelia in vitro and in vivo. J. Pharm. Sci. 90 (2001) 38–46] as well as chitosan-EDTA conjugates [Chitosan-Conjugates with Acidic Chelate-Complex Forming Agents; WO9831712A2; Inventor(s): Bernkop-Schnürch Andreas and Paikl Christina].

Chitosan and chitosan derivatives according to the state of the art have their drawbacks with respect to their viscoelastic and gelling properties on the one hand and with their handling properties in pharmaceutical preparation processes, especially on an industrial scale on the other hand. It is therefore an object of the present invention to provide polymers, especially chitosan derived polymers, with superior properties.

Therefore, the present invention provides polymeric compounds as defined in any one of claims 1 to 5. Such polymers may be preferably produced by a method according to any one claims 6, 7 or 19. Preferred uses of the present polymers are provided by the subject matter of claims 8 to 18.

With the chemical modification of chitosan polymers according to the present invention, polymeric compounds with favourable properties and surprising handling characteristics are provided.

The term "polymer" as used herein relates to molecules having a molecular weight of at least 1 kDa, preferably at least 50 kDa, especially at least 200 kDa, and comprising at least 5, preferably at least 20, especially at least 100, moieties of an identifiable monomer, preferably a carbohydrate (sugar) monomeric entity (thereby defining a polysaccharide), especially a monomeric entity being derived from a glucose (glucosamine) structure having the N-substituents at the C-2 atom as described herein, and having at least 2, preferably at least 10, especially at least 50, thio-amidine-conjugated sugar structure as defined in claim 1. Alkyl is preferably a linear or branched $C_1$–$C_{10}$ group; "aryl" is preferably a substituted or non-substituted aromatic ring without heteroatoms.

By the reaction of chitosan with iminothiolactones such as 2-iminothiolane thiol-substructures are covalently immobilized on the polymer as well as the cationic character of the polymer is strongly improved. The chemical structure of a preferred modified chitosan is illustrated in FIG. 1. The purification of chitosan-thio-amidine conjugates can preferably be performed via dialysis or precipitation of the polymer from solutions. Surprisingly, the viscoelastic features of chitosan were strongly improved by this chemical modification. Aqueous gels of this chitosan-derivative showed under inert conditions a low viscosity, whereas it increased more than 500-fold in the presence of air. The reason for this effect is the formation of disulfide bonds within the polymer leading to a crosslinking of polymer chains. Furthermore, modified chitosan adheres excellent on skin and hair mediated by the formation of disulfide bonds between the thiol groups of the polymer and cysteine subunits of surface proteins. These properties render thiolated chitosans to promising compounds for hairgels or make-ups, which should stabilize their selves after application avoiding a smearing and dissolution. From the pharmaceutical point of view, the polymers according to the present invention offer the advantage of in situ gelling excipients for e.g. eye drops. Such eye drops can be easily instilled at low viscosity, subsequently becoming highly viscous on the ocular surface mediated by an oxidation process on air. Due to this improved viscosity on the ocular surface the polymer and therefore also the incorporated drug remain for a prolonged period of time on the target tissue, which will strongly improve the therapeutic effect. Moreover, in case of tissue engineering polymers based on the invention described herein are highly beneficial. Cells can be homogenized with aqueous solutions of such a chitosan derivative at low viscosity ex vivo. After injection in the body or pouring the suspension in moulds, the polymer/cell mixture becomes solid due to access to oxygen (or other suitable oxidizing agents) providing a stable scaffold for cell proliferation. Moreover, due to the excellent in situ gelling properties of chitosan-thio-amidine conjugates they can be used as vitreous substitutes, which are injected in form of aqueous solutions becoming solid by oxidation in the eye. Furthermore, the polymers described herein are useful as coating material of stents providing a controlled release of embedded drugs.

The present invention therefore also encompasses such implants, scaffolds, stents, coats and other products, especially pharmaceutical or cosmetic products, comprising or being made of the polymers according to the present invention.

The present invention is further described in the following examples and in the figures, yet without being limited thereto.

EXAMPLES

Example 1

Synthesis of chitosan-4-thio-butyl-amidine Conjugates

Figure 1:
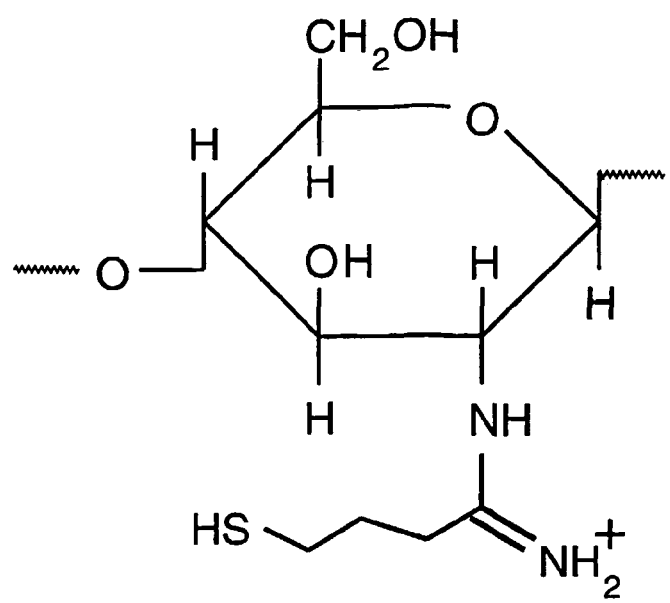
FIG. 1 shows the chemical structure of a preferred polymer according to the present invention.

Chitosan with a molecular mass of ~150 kDa and a degree of deacetylation of 85% was dissolved in 1% acetic acid in a final concentration of 0.2% (m/v). After the addition of 2-iminothiolane HCl (Traut's reagent) in a final concentration of 0.7 mg/ml the oxygen in the solution is removed by bubbling with nitrogen for two hours. The pH is adjusted to pH 6.5 with 1 M NaOH and the reaction allowed to proceed for eight hours under inert conditions at room temperature. The resulting chitosan-4-thio-butyl-amidine conjugate (see FIG. 1) is isolated by dialysis against 2 mM HCl and then against demineralized water. The isolated polymer is lyophilized. The conjugate produced by this method exhibits 0.5±0.2 mMol immobilized thiol-groups per gram polymer.

Example 2

Synthesis of chitosan-4-thio-butyl-amidine Conjugate Derivatives

Chitosan with a molecular mass of ~150 kDa and a degree of deacetylation of 85% was dissolved in 1% acetic acid in a final concentration of 0.2% (m/v). After the addition of 5-methyl-2-iminothiolane HCl, 5,5-dimethyl-2-iminothiolane HCl, 5-phenyl-2-iminothiolane HCl or 4-methoxy-2-iminothiolane HCl in a final concentration of 1 mg/ml the oxygen in the solution is removed by bubbling with nitrogen for two hours. The pH is adjusted to pH 6.0 with 1 M NaOH and the reaction allowed to proceed for eight hours under inert conditions at room temperature. The resulting chitosan-4-thio-butyl-amidine conjugate derivatives are isolated by dialysis against 2 mM HCl and then against demineralized water. The isolated polymer is lyophilized. The conjugates produced by this method exhibit between 0.02 and 0.6 mMol immobilized thiol-groups per gram polymer.

Example 3

Formation of Disulfide Bonds

Figure 2:
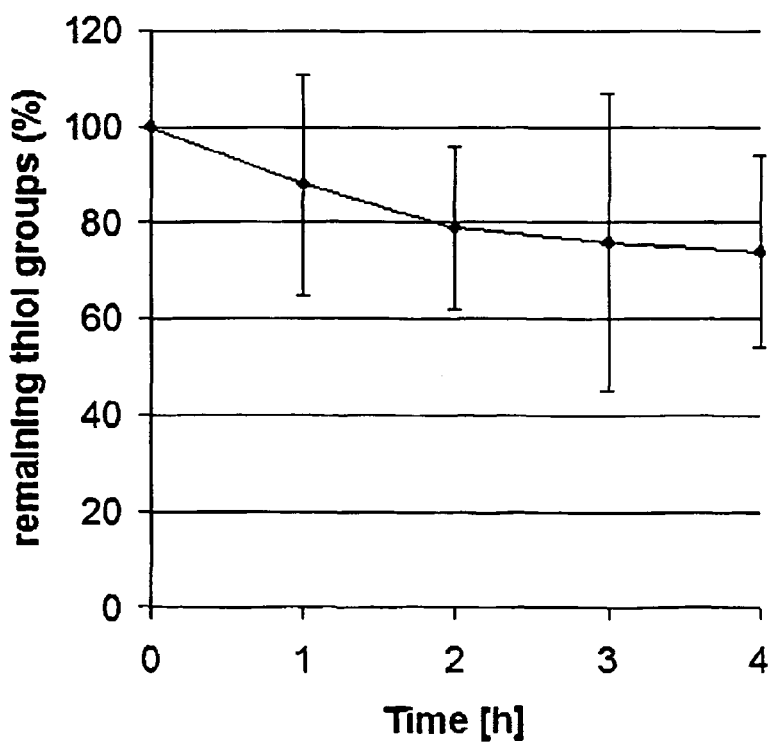
FIG. 2 shows the concentration of remaining thiol-groups after formation of disulfide bonds.

The formation of disulfide bonds within thiolated chitosan was determined as follows. Chitosan-4-thio-butyl-amidine conjugate was dissolved in 80 mM acetate buffer pH 6.5 in a final concentration of 0.5% (m/v). Thereafter, the pH value of the polymer solution was readjusted to pH 6.5 by the addition of 1 M NaOH. The reaction mixture was incubated at 37° C. and aliquots were withdrawn at the beginning of the experiment and then every hour. The concentration of remaining thiol-groups in these samples was determined via Ellman's reagent [5,5,-dithiobis(2-nitrobencoic acid)]. Results of this study are shown in FIG. 2. They demonstrate a decrease in the remaining thiol groups i.e. the formation of disulfide bonds within the polymeric network as a function of time. Within 4 hours, approximately 25% of all thiol groups were oxidized to disulfide bonds.

Example 4

Increase in Viscosity

Figure 3:
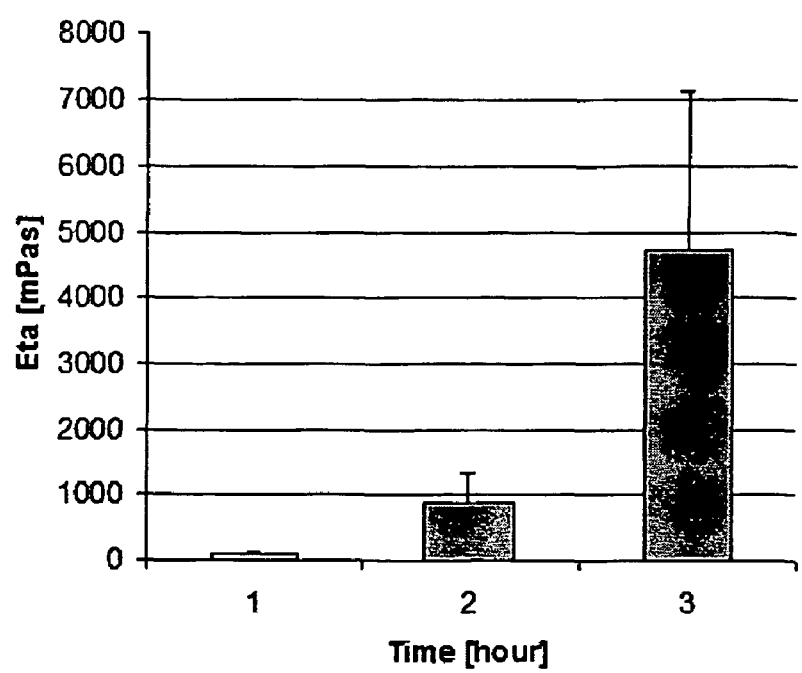
FIG. 3 shows the increase of viscosity due to the formation of disulfide bonds.

Increase in viscosity due to the formation of disulfide bonds was determined utilizing a viscometer (cone/plate). The chitosan-4-thio-butyl-amidine conjugate was dissolved in 80 mM phosphate buffer pH 6.0 in a final concentration of 1.5% (m/v). The increase in viscosity of this solution was measured at time-points 0, 5 and 20 hours via a flow curve. The results of this study are shown in FIG. 3. They demonstrate a significant increase in viscosity of the polymer solution as a function of time. After an incubation period of 20 hours the viscosity of the polymer solution was approximately 50-fold higher than at the starting point. The advantage of these in-situ gelling properties is that polymer solutions can be applied in their liquid form becoming solid after application. In the cosmetic field, for instance, make-ups can be applied in liquid form becoming stable on the skin after some minutes.

Example 5

Preparation of a Formulation for a Hair Gel

First, 2 g of chitosan-4-thio-butyl-amidine conjugate is dissolved in 200 ml of demineralised, oxygen-free water. The pH-value of the solution was adjusted to pH 7.0 by the addition of NaOH. After the addition of 80 ml isopropylalcohol, the resulting transparent gel is filled up under inert conditions in single unit vessels of 30 ml.

Example 6

Preparation of a Formulation for a Make-up

First, 4 g of chitosan-4-thio-butyl-amidine conjugate were dissolved in 200 ml of demineralized, oxygen-free water. Thereafter, 60 ml of a color-pigment solution (30% suspension; Biotic Phocea, Marseille, France) is added. After the removal of remaining oxygen by vacuum, demineralized water is added in order to achieve a final volume of 200 ml and the pH-value is adjusted to 7.0. The make-up formulation is filled up under inert conditions in single unit vessels of 1 ml.

Example 7

Preparation of a Pharmaceutical Formulation for Timolol Eye Drops

Timolol HCl (3-tert-butylamino-1-[(4-morpholino-1,2,5-thiadiazol-3-yl)oxy]-2-propanol) is a beta-blocker for treatment of glaucoma. The drug is dissolved in a final concentration of 0.5% (m/v) in 20 mM acetate buffer pH 5.2. After the addition of chitosan-4-thio-butyl-amidine conjugate in a final concentration of 0.1% (m/v) and a preservative in a final concentration of 0.03% (m/v), the pH-value is readjusted to pH 5.2. Remaining oxygen is removed by bubbling the solution with nitrogen. The resulting eye drops are filled up under inert conditions in multiple unit vessels of 10 ml. The vessels are than sealed with an aluminium-foil.

Example 8

Preparation and Characterization of Tablets Containing Clotrimazole

Figure 4:
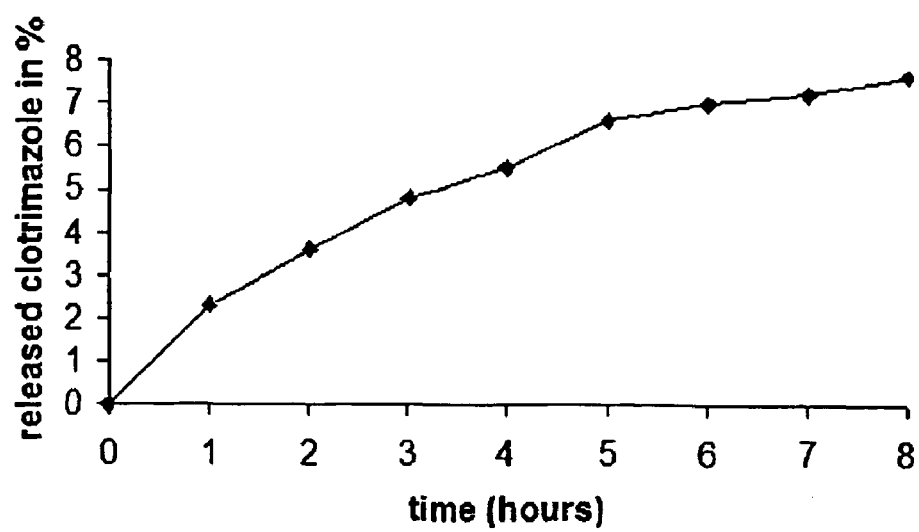
FIG. 4 shows the amount of clotrimazole released from tablets comprising a polymer according to the present invention.

First, 500 mg of chitosan-4-thio-butyl-amidine conjugate 0.5% was hydrated in 40 ml of demineralized water and homogenized with 100 mg of clotrimazole dissolved in 2 ml of dioxane. The mixture was frozen at −20° C. and lyophilized. Tablets were compressed out of the lyophilized polymer/clotrimazole mixture as described above. The in vitro drug release out of this drug delivery system was analyzed. The dosage form was placed in a beaker (Schott Duran 25 ml, Germany) containing 6 ml of release medium (80 mM acetate buffer pH 6.0/dioxane; 7+3). The closed vessels were placed on an oscillating water bath and incubated at 37° C. Sink conditions were maintained during the study. Aliquots of 400 µl were withdrawn every hour for 8 hours. The medium was replaced with an equal volume of release medium. Released clotrimazole was assayed by measuring the absorbance photometrically at 256 nm. Concentrations were calculated by interpolation from a standard curve. Results of release studies are shown in FIG. 4. They demonstrate that a controlled and sustained drug release can be guaranteed out of the delivery system.

Example 9

Tissue Engineering

Preparation of Scaffolds (Method I)

Lyophilised chitosan-4-thio-butyl-amidine conjugate was rehydrated with demineralised water to obtain a 3% (m/v) polymer gel. The obtained gel was sterilised by autoclaving (10 min., 121° C.) and stored at room temperature under sterile conditions until further use.

Preparation of Scaffolds (Method II)

Lyophilised chitosan-4-thio-butyl-amidine conjugate was sterilised in the following manner: small sheets of the lyophilised thiolated chitosan were incubated with 96% (v/v) EtOH for one hour followed by an incubation with 70% (v/v) isopropylalcohol for 48 hours. For further storage 70% (v/v) EtOH was used.

Cell Culture Studies

Cell culture studies were conducted in 24-well culture plates. Untreated culture wells served as control. Sheets of chitosan-4-thio-butyl-amidine conjugate were cut into 5×5 mm pieces, air dried in the culture vessel and rinsed three times with PBS (phosphate buffered saline, pH 7.4; Life Technologiesâ) to adjust the pH to 7.4. Gels were liquefied and drops (approximately 5 mm in diameter) were transferred into the culture plates. L-929 cells (mouse fibroblasts) were resuspended in 10 µl DMEM (Life Technologiesâ)+ 10% FCS (Life Technologiesâ) and 1×104 cells were seeded onto each chitosan-4-thio-butyl-amidine conjugate containing vessel as well as onto control vessels. After two hours of incubation, 750 µl of medium were added. The cell growth on the scaffolds was investigated with a microscope every two days. Results demonstrated a fast and densely growth of the cells on the novel scaffold material.

Features of the polymers according to the present invention:

1. Acidic aqueous solutions of chitosan-thio-amidine conjugates represent transparent clear gels.
2. Aqueous solutions of chitosan-thio-amidine conjugates become solid in the presence of oxygen by the formation of disulfide bonds.
3. Preparations of chitosan-thio-amidine conjugates exhibit strong in situ gelling properties.
4. Under inert condition the immobilized thiol groups remain stable on chitosan-thio-amidine conjugates.
5. Chitosan-thio-amidine conjugates exhibit thiol side chains and a stronger cationic character than chitosan.

The invention claimed is:

1. A composition comprising a polymeric compound comprising the following substructure within its overall structure:

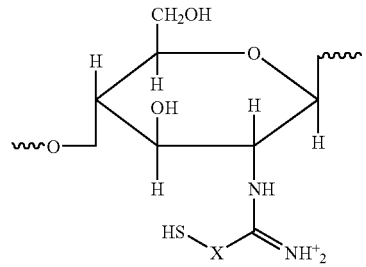

wherein X=—$CR_1R_2$—$CR_1R_2$—$CR_1R_2$—$CR_1R_2$—$CR_1R_2$—$CR_1R_2$—, —$CR_1R_2$—$CR_1R_2$—$CR_1R_2$—$CR_1R_2$—$CR_1R_2$—, —$CR_1R_2$—$CR_1R_2$—$CR_1R_2$—$CR_1R_2$—, —$CR_1R_2$—$CR_1R_2$—$CR_1R_2$—, —$CR_1R_2$—$CR_1R_2$— or —$CR_1R_2$—, wherein $R_1$ and $R_2$ are each or together a substituent selected from hydrogen, —OH, —SH, —O—$CH_3$; —O—$CH_2$—$CH_3$, —O—$CH(CH_3)_2$, —O—$CH_2$—$CH_2$—$CH_3$, —OOC—$CH_3$, —OOC—$CH_2$—$CH_3$, —OOC—$CH_2$—$CH_2$—$CH_3$, =O, —Cl, —Br, —I, alkyl, aryl or O-aryl.

2. The composition of claim 1, wherein X=—$CH_2$—$CH_2$—$CH_2$—, —$CH_2$—$CH_2$—, —$CH_2$—, —$CH_2$—CRH—$CH_2$— (R=alkyl-, aryl or O-aryl-residue), or —$CH_2$—CO—$CH_2$—.

3. The composition of claim 1, wherein the polymeric compound is further defined as a Chitosan derivative.

4. The composition of claim 1, having a concentration of covalently linked thiol groups of between 10 and 4200 µmol per gram polymeric compound.

5. The composition of claim 4, having a concentration of covalently linked thiol groups of between 50 and 2000 µmol per gram polymeric compound.

6. The composition of claim 1, wherein the polymeric compound is further defined as a polymeric compound that, in an aqueous 1% solution, exhibits a more than 5-fold increase in viscosity due to oxidation of the polymeric compound.

7. The composition of claim 6, wherein the polymeric compound is further defined as a polymeric compound that, in an aqueous 1% solution, exhibits a more than 50-fold increase in viscosity due to oxidation of the polymeric compound.

8. The composition of claim 1, further defined as a cosmetic preparation.

9. The composition of claim 1, further defined as a hair gel.

10. The composition of claim 1, further defined as a make-up compound.

11. The composition of claim 1, further defined as a pharmaceutical compound.

12. The composition of claim 1, further defined as an eye drop preparation.

13. The composition of claim 1, further defined as a vitreous substitute.

14. The composition of claim 1, further defined as a stent coating material.

15. The composition of claim 1, further defined as a tissue engineering material.

16. The composition of claim 1, further defined as a cell culturing material.

17. The composition of claim 1, further defined as comprised in a scaffold comprising biological cells or tissue.

18. The composition of claim 17, further defined as comprised in an implant.

19. A method for producing a polymeric compound comprising the following substructure within its overall structure:

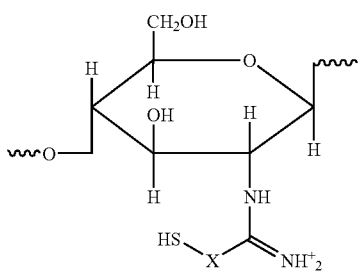

wherein X=—$CR_1R_2$—$CR_1R_2$—$CR_1R_2$—$CR_1R_2$—$CR_1R_2$—$CR_1R_2$—, —$CR_1R_2$—$CR_1R_2$—$CR_1R_2$—$CR_1R_2$—$CR_1R_2$—, —$CR_1R_2$—$CR_1R_2$—$CR_1R_2$—$CR_1R_2$—, —$CR_1R_2$—$CR_1R_2$—$CR_1R_2$—, —$CR_1R_2$—$CR_1R_2$— or —$CR_1R_2$—, wherein $R_1$ and $R_2$ are each or together a substituent selected from hydrogen, —OH, —SH, —O—$CH_3$; —O—$CH_2$—$CH_3$, —O—$CH(CH_3)_2$, —O—$CH_2$—$CH_2$—$CH_3$, —OOC—$CH_3$, —OOC—$CH_2$—$CH_3$, —OOC—$CH_2$—$CH_2$—$CH_3$, =O, —Cl, —Br, —I, alkyl, aryl or O-aryl, the method comprising reacting chitosan with an iminothiolactone of the following general structure:

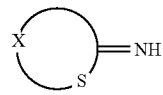

20. The method of claim 19, wherein said iminothiolactone is 2-iminothiolane.

21. The method of claim 19, further comprising formulating the compound into a cosmetic preparation.

22. The method of claim 19, further comprising formulating the compound into a hair gel.

23. The method of claim 19, further comprising formulating the compound into a make-up compound.

24. The method of claim 19, further comprising formulating the compound into a pharmaceutical compound.

25. The method of claim 19, further comprising formulating the compound into an eye drop preparation.

26. The method of claim 19, further comprising formulating the compound into a vitreous substitute.

27. The method of claim 19, further comprising formulating the compound into a stent coating material.

28. The method of claim 19, further comprising formulating the compound into a tissue engineering material.

29. The method of claim 19, further comprising formulating the compound into a cell culturing material.

30. The method of claim 19, further comprising formulating the compound into a scaffold comprising the compound and biological cells or tissue.

31. The method of claim 30, wherein the scaffold is further defined as an implant.

* * * * *